(12) United States Patent
Higashino et al.

(10) Patent No.: US 11,249,076 B2
(45) Date of Patent: Feb. 15, 2022

(54) TEST DEVICE, REACTION APPARATUS AND REACTIVE TEST METHOD

(71) Applicant: OTSUKA PHARMACEUTICAL CO., LTD., Tokyo (JP)

(72) Inventors: Kusunoki Higashino, Osaka (JP); Yasuhiro Sando, Amagasaki (JP); Kenichi Miyata, Amagasaki (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1081 days.

(21) Appl. No.: 14/464,971

(22) Filed: Aug. 21, 2014

(65) Prior Publication Data

US 2015/0050748 A1    Feb. 19, 2015

Related U.S. Application Data

(62) Division of application No. 13/010,142, filed on Jan. 20, 2011, now abandoned.

(51) Int. Cl.
| | | |
|---|---|---|
| *G01N 33/543* | (2006.01) | |
| *B01F 5/06* | (2006.01) | |
| *B01F 11/00* | (2006.01) | |
| *B01F 15/00* | (2006.01) | |
| *B01F 5/10* | (2006.01) | |
| *B01F 11/02* | (2006.01) | |
| *B01F 13/00* | (2006.01) | |
| *B01L 3/00* | (2006.01) | |

(52) U.S. Cl.
CPC ..... *G01N 33/54306* (2013.01); *B01F 5/0615* (2013.01); *B01F 5/102* (2013.01); *B01F 11/0071* (2013.01); *B01F 11/0266* (2013.01); *B01F 13/0059* (2013.01); *B01F 15/00876* (2013.01); *G01N 33/54366* (2013.01); *B01F 2005/0633* (2013.01); *B01F 2005/0636* (2013.01); *B01L 3/50273* (2013.01); *B01L 2300/088* (2013.01); *B01L 2400/0439* (2013.01); *B01L 2400/0481* (2013.01); *B01L 2400/0487* (2013.01); *B01L 2400/086* (2013.01)

(58) Field of Classification Search
CPC .............. B01F 11/0071; B01F 11/0266; B01F 13/0059; B01F 15/00876; B01F 2005/0633; B01F 2005/0636; B01F 5/0615; B01F 5/102; B01L 2300/088; B01L 2400/0439; B01L 2400/0481; B01L 2400/0487; B01L 2400/086; B01L 3/50273; G01N 33/54306; G01N 33/54366
USPC ....................................................... 436/501
See application file for complete search history.

(56) References Cited

U.S. PATENT DOCUMENTS

| | | | |
|---|---|---|---|
| 6,008,893 A | 12/1999 | Roos et al. | |
| 7,763,453 B2 | 7/2010 | Clemmens | |
| 10,921,313 B2* | 2/2021 | Puntambekar | ..... G01N 33/5302 |
| 2003/0102215 A1* | 6/2003 | Bukshpan | ........ G01N 27/44795 204/459 |
| 2003/0124599 A1* | 7/2003 | Chen | ..................... B01J 19/0046 506/39 |
| 2003/0138941 A1* | 7/2003 | Gong | ..................... B01L 3/5027 435/287.2 |
| 2004/0167733 A1* | 8/2004 | MacDonald | ........... G01R 13/28 702/72 |
| 2005/0180891 A1 | 8/2005 | Webster | |
| 2006/0068412 A1* | 3/2006 | Tang | ................. G01N 33/54373 435/6.11 |
| 2006/0110725 A1* | 5/2006 | Lee | ................... B01L 3/502753 435/5 |
| 2007/0183935 A1* | 8/2007 | Clemmens | .......... B01F 11/0071 422/400 |
| 2008/0118972 A1* | 5/2008 | Yoo | ....................... B01J 20/3204 435/270 |
| 2008/0202933 A1* | 8/2008 | Hu | ..................... B01L 3/502715 204/451 |
| 2009/0052273 A1* | 2/2009 | Sarvazyan | .......... B01F 13/0059 366/116 |
| 2009/0176312 A1* | 7/2009 | Selinfreund | .............. B01L 7/52 436/164 |
| 2010/0124142 A1* | 5/2010 | Laugharn, Jr. | ...... B01L 3/50273 366/108 |
| 2010/0248278 A1 | 9/2010 | Pouteau | |
| 2011/0070581 A1* | 3/2011 | Gupta | .............. G01N 33/56972 435/5 |

(Continued)

FOREIGN PATENT DOCUMENTS

| | | |
|---|---|---|
| JP | 10-170495 A | 6/1998 |
| JP | 2002-214241 A | 7/2002 |
| JP | 2002-540405 A | 11/2002 |

(Continued)

OTHER PUBLICATIONS

Oxford Dictionaries, https://en.oxforddictionaries.com/definition/circulation, retrieved Nov. 20, 2017, p. 1.*

(Continued)

*Primary Examiner* — Ann Montgomery

(74) *Attorney, Agent, or Firm* — Sughrue Mion, PLLC

(57) ABSTRACT

A test device having a micro flow channel including a reaction part where a reactant that is reactive to a tested chemical dispersed in a tested fluid is fixed, and at least one actuator for actuating the tested fluid to move in at least one of two opposite sides of the micro flow channel so as to homogenize a density distribution of the tested chemical in the tested fluid. The tested fluid is sent in the micro flow channel a plurality of times.

5 Claims, 6 Drawing Sheets

(56) References Cited

U.S. PATENT DOCUMENTS

2011/0096327 A1* 4/2011 Papautsky ................ B03B 5/32
356/335

FOREIGN PATENT DOCUMENTS

| | | |
|---|---|---|
| JP | 2004-321063 A | 11/2004 |
| JP | 2005-28531 A | 2/2005 |
| JP | 2005-134372 A | 5/2005 |
| JP | 2006-90717 A | 4/2006 |
| JP | 2006-142210 A | 6/2006 |
| JP | 2006-284323 A | 10/2006 |
| JP | 2007-209236 A | 8/2007 |
| JP | 2008-212882 A | 9/2008 |
| JP | 2010-243419 A | 10/2010 |
| WO | 0057192 | 9/2000 |

OTHER PUBLICATIONS

Notification of Reasons for Refusal for Japanese Patent Application No. 2009-094568, dated Nov. 20, 2012, with English translation.

* cited by examiner

TEST DEVICE, REACTION APPARATUS AND REACTIVE TEST METHOD

CROSS REFERENCE TO RELATED APPLICATIONS

The present application is a divisional application of U.S. patent application Ser. No. 13/010,142, filed on Jan. 20, 2011, the entire contents of which are incorporated herein by reference. The Ser. No. 13/010,142 application claimed the benefit of the date of the earlier filed Japanese Patent Application No. JP2009-094568, filed Apr. 9, 2009, priority to which is also claimed herein, and the contents of which are also incorporated by reference herein.

BACKGROUND OF THE INVENTION

1. Field of the Invention

The present invention relates to a test device, a reaction apparatus and a reactive test method, and more particularly to a test device, a reaction apparatus and a reactive test method for sending a tested fluid containing a tested chemical, such as an antigen, in a micro flow channel to cause the tested chemical to react to a reactant, such as an antibody.

2. Description of Prior Art

FIG. 9 shows a conventional test device comprising a micro flow channel to subject various kinds of antigens in blood plasma to reaction to antibodies. In the apparatus shown by FIG. 9, there is a reaction part 51 wherein a reactant is fixed at the bottom of a micro flow channel 50, and a tested fluid with a tested chemical T dispersed therein is sent in the micro flow channel 50 from one side to the other side (see arrow "A"). In the reaction part 51, the tested chemical T reacts only around the surface of a solid-phase layer of the reactant. Therefore, the tested chemical T flowing in the upper part of the micro flow channel 50 passes through the micro flow channel 50 without contributing to the reaction, and the reaction efficiency is bad.

As a measure to improve the reaction efficiency, it may be possible to reciprocate the tested fluid in the micro flow channel so that the part of the tested chemical that did not react first can be sent back to the reaction part. For example, Japanese Patent Laid-Open Publication No. 2006-90717 teaches that a tested fluid is sent back and forth to a reaction part by use of a fluid sending means such as a pipette. Japanese Patent laid-Open Publication No. 2002-540405 discloses a system and a method for permitting reversible and controllable flowing of a tested fluid.

Even in a back-and-forth fluid sending method as described above, the following problems still remain unsolved. In order to improve the reaction efficiency by sending a tested chemical closer to a reaction part, the micro flow channel is preferably as shallow as possible within a range not to dispute the fluid sending, and preferably, the depth of the micro flow channel is equal to or less than 1 mm. Also, in order to prevent the pressure of fluid sending in the micro flow channel from rising excessively, the flow rate of the tested fluid is preferably less than several tens of millimeters per second. In such a fluid sending system, the fluid moves in laminar flow because Reynolds number is low. Accordingly, even by reciprocating a tested fluid in the fluid sending system, a tested chemical does not blend in the tested fluid, and the part of the tested chemical flowing in the upper part of the micro flow channel keeps flowing in the upper part. Therefore, even if the tested fluid is sent back and forth many times, the tested chemical flowing in the upper part does not contribute to reaction.

The Reynolds number is an index value that is generally used in the field of fluid dynamics. The followings are known: if the Reynolds number is greater than 2000, the flow is turbulent; and if the Reynolds number is equal to or less than 2000, the flow is laminar. When the solvent is water based and when the size of the micro flow channel and the flow rate therein are as above, the Reynolds number is generally less than 100, and accordingly, the flow is laminar. Therefore, the reaction efficiency does not improve unless any special measure is taken.

SUMMARY OF THE INVENTION

An object of the present invention is to provide a test device, a reaction apparatus and a reactive test method that permit improved reaction efficiency in a micro flow channel of a conventional size.

In order to attain the object, a test device according to a first aspect of the present invention comprises: a micro flow channel including a reaction part where a reactant that is reactive to a tested chemical dispersed in a tested fluid is fixed; and at least one actuator for actuating the tested fluid to move in at least one of two opposite sides of the micro flow channel so as to homogenize a density distribution of the tested chemical in the tested fluid; wherein the tested fluid is sent in the micro flow channel a plurality of times.

A reaction apparatus according to a second aspect of the present invention comprises: a test device comprising a reaction part in a micro flow channel, a reactant that is reactive to a tested chemical dispersed in a tested fluid being fixed in the reaction part; a fluid sender for sending the tested fluid in the micro flow channel a plurality of times; and at least one actuator for actuating the tested fluid to move in at least one of two opposite sides of the micro flow channel so as to homogenize a density distribution of the tested chemical in the tested fluid.

A reactive test method according to a third aspect of the present invention comprises the steps of; sending a tested fluid in a micro flow channel a plurality of times, the micro flow channel including a reaction part where a reactant that is reactive to a tested chemical dispersed in the tested fluid is fixed; and actuating the tested fluid to move in at least one of two opposite sides of the micro flow channel so as to homogenize a density distribution of the tested chemical in the tested fluid.

In the present invention, "to homogenize a density distribution of the tested chemical in the tested fluid" does not necessarily mean to completely homogenize the density distribution of the tested chemical in the tested fluid, and "actuating the tested fluid to move so as to homogenize the density distribution of the tested chemical in the tested fluid" means actuating the tested fluid to move so that the density distribution of the tested chemical in the tested fluid will be more even.

BRIEF DESCRIPTION OF THE DRAWINGS

This and other objects and features of the present invention will be apparent from the following description with reference to the accompanying drawings, in which.

DETAILED DESCRIPTION OF THE PREFERRED EMBODIMENTS

Figure 1A:
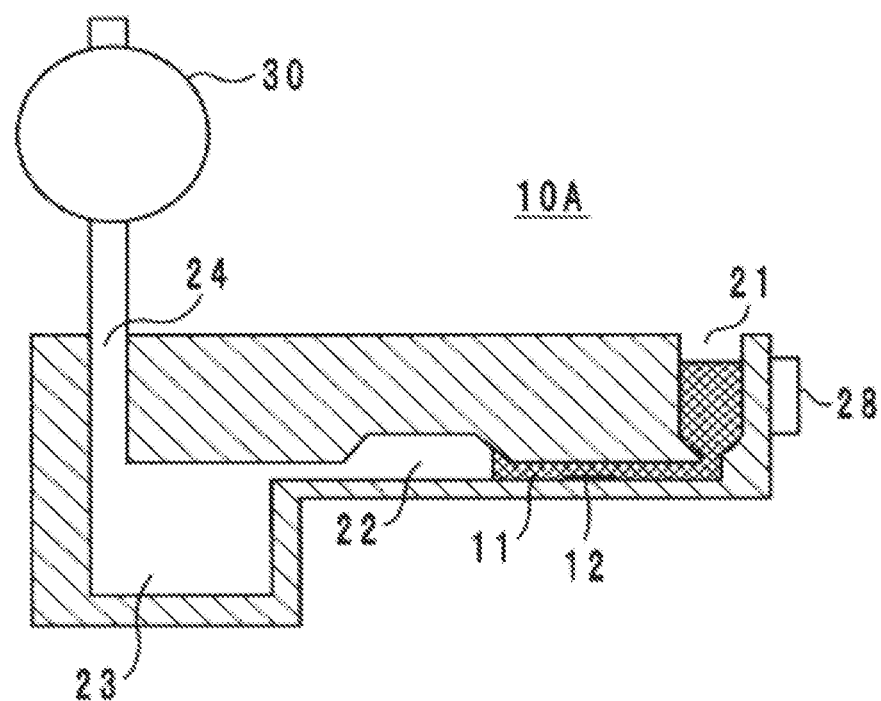
FIGS. 1A and 1B are a sectional view of a test device according to a first embodiment of the present invention.

Test devices, reaction apparatuses and reactive test methods according to some embodiments of the present invention are hereinafter described with reference to the accompanying drawings. In the drawings, the same parts and the same members are provided with the same reference numbers, and repetitious descriptions thereof are omitted.

First Embodiment; See FIG. 1

Figure 1B:
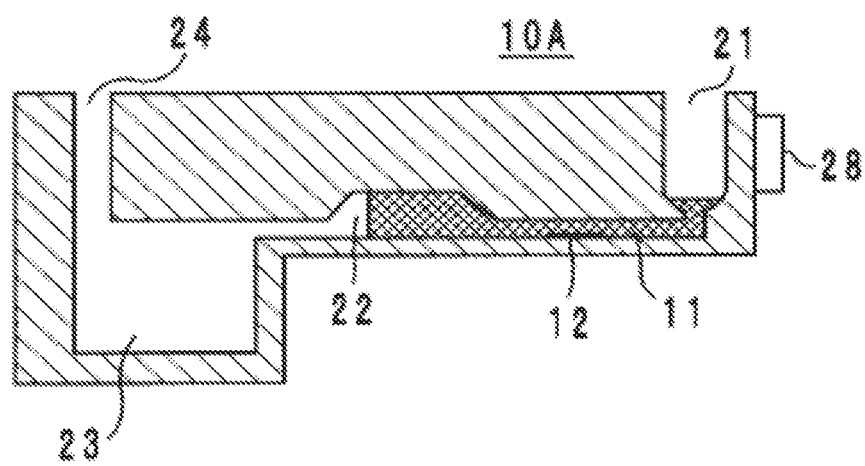

A test device 10A according to a first embodiment of the present invention, as shown in FIGS. 1a and 1b, comprises a micro flow channel 11, a first reservoir 21 disposed at one end of the micro flow channel 11, a second reservoir 22 disposed at the other end of the micro flow channel 11, a waste reservoir 23 connected directly to the second reservoir 22, and an air inlet/outlet 24. An air pump 30 is connected to the air inlet/outlet 24. The reservoirs 21 and 22 have inner volumes larger than the volume of a tested fluid to be sent (shown by cross-hatching in FIG. 1). In the first embodiment, a combination of the test device 10A and the air pump 30 is referred to as a reaction apparatus.

In the micro flow channel 11, a reaction part 12 wherein a reactant that is reactive to a tested chemical dispersed in the tested fluid is fixed is provided. An oscillator 28 is adhered to a wall of the first reservoir 21. The oscillator 28 is to stir and blend the tested fluid in the first reservoir 21 so that the density of the tested chemical in the tested fluid will be even. For example, a PZT (a piezoelectric actuator made of lead zirconate titanate) is suited as the oscillator 28.

The tested fluid is, for example, blood plasma obtained by centrifugation of blood collected from a biological object. In this case, various kinds of antigens in the blood are the tested chemicals, and antibodies specifically reactive to the antigens are the reactants fixed in the reaction part 12.

In the test device 10A according to the first embodiment 10A, the tested fluid is first poured into the reservoir 21. Next, by operation of the air pump 30, the tested fluid is sent toward the reservoir 22, that is, sent from the state shown by FIG. 1a to the state shown by FIG. 1b, and further, the tested fluid is sent back to the state shown by FIG. 1a. In this way, the tested fluid is reciprocated in the micro flow channel 11 and passes through the reaction part 12 a plurality of times, and in the meantime, the antigens react to the antibodies. While the tested fluid is stored in the reservoir 21, the oscillator 28 is operated. Thereby, the tested fluid is stirred so that the antigens can be dispersed in the tested fluid evenly.

In the first embodiment, in the reservoir 21 disposed at one side of the micro flow channel 11, the density distribution of antigens in the tested fluid is homogenized, and the tested fluid is sent back and forth in the micro flow channel 11 a plurality of times. Consequently, the rate of antigens reacting to the antibodies in the reaction part 12 increases, and the reaction efficiency is improved.

Since the inner volumes of the reservoirs 21 and 22 are larger than the volume of the tested fluid, there is no fear that the tested fluid may flow out of the reservoirs 21 and 22 even if the entire tested fluid is sent in the micro flow channel 11 reciprocally. The bottom of the reservoir 21 is bowl shaped, and the upper portion of the reservoir 21 is wide open. Therefore, when the tested fluid in the reservoir 21 is vibrated by the oscillator 28, the tested fluid is easy to move, and the stirring efficiency is good. With respect to the upper opening of the reservoir 21, the area of the upper opening shall be set as follows so as to obtain a sufficient effect of a wide opening. Assuming that there is a sphere having a volume equal to that of the tested fluid, the upper opening of the reservoir 21 shall be set equal to or greater than 1/10 of the area of the planar projection of the sphere.

The vibration frequency of the oscillator 28 may be set to any value. It is, however, preferred for the stirring efficiency that the vibration frequency of the oscillator 28 is equal to or nearly equal to the resonance frequency of the tested fluid. The resonance frequency of the tested fluid may vary depending on the volume of the tested fluid, and therefore, it is preferred that the drive frequency of the oscillator 28 is changed in accordance with changes in the volume of the tested fluid in the reservoir 21 due to the fluid sending. Alternatively, the drive frequency of the oscillator 28 may be waved to cause the vibration frequency of the oscillator 28 to come in resonance with the tested fluid intermittently. In this case, random motion of the tested fluid is induced, and mixing of the antigens can be promoted.

After the tested fluid is reciprocated a predetermined number of times, the tested fluid is sucked up by the air pump 30 and is thrown away to the reservoir 23. Next, a cleaning solution is dropped in the reservoir 21 and sent in the micro flow channel 11 by the air pump 30, so that non-reacted antigens remaining in the reaction part 12 are removed. Thereafter, the surface of the reaction part 12 is detected optically by a detector (not shown), and immune reactions between the antigens and the antibodies can be recognized from changes in the optical characteristics. Such a way of recognizing an immune reaction is known, and a description thereof is omitted.

Second Embodiment; See FIG. 2

Figure 2:
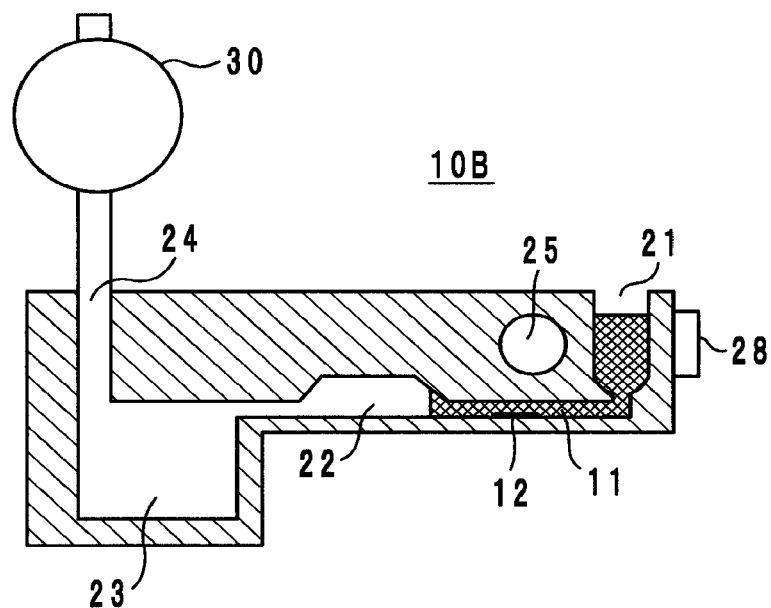
FIG. 2 is a sectional view of a test device according to a second embodiment of the present invention.

A test device 10B according to a second embodiment of the present invention, as shown in FIG. 2, is basically of the same structure as the test device 10A according to the first embodiment. In the test device 10B according to the second embodiment, a cavity resonator 25 is provided near the reservoir 21. The test device 10B according to the second embodiment operates in the same way as the test device 10A according to the first embodiment and has the same advantages as the test device 10A. In the test device 10B, especially the cavity resonator 25 amplifies the resonance by the oscillator 28, thereby resulting in an improvement in the stirring efficiency of the tested fluid.

Third Embodiment; See FIG. 3

Figure 3:
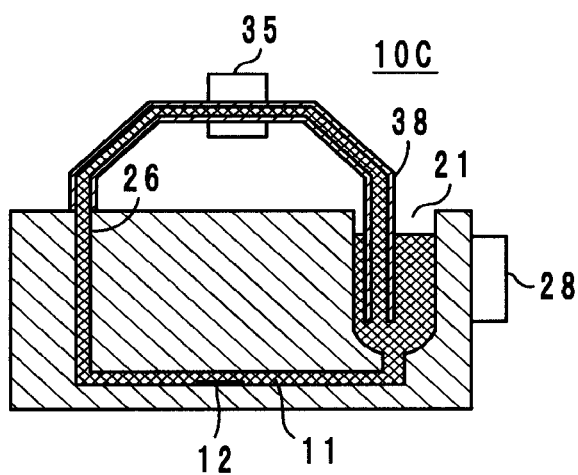
FIG. 3 is a sectional view of a test device according to a third embodiment of the present invention.
Figure 4:
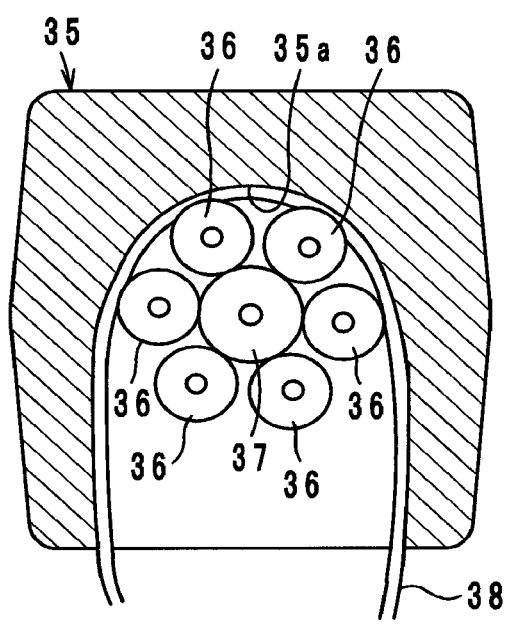
FIG. 4 is a front view of a pump used in the third embodiment.

A test device 10C according to a third embodiment, as shown in FIG. 3, has a peristaltic tube pump 35 instead of the air pump 30. This tube pump 35 has a tube 38, a center roller 37 and a plurality of rollers 36 around the center roller 37, and the tube 38 is nipped between a wall 35a and the rollers 36. The rollers 36 are caused to rotate by the center roller 37, and thereby, the tested fluid in the tube 38 is sent in a direction in accordance with the rotations of the rollers 36.

The test device 10C has a reservoir 21 provided with an oscillator 28 and a micro flow channel 11 including a reaction part 12. One end of the tube 38 is in the reservoir 21, and the other end of the tube 38 is connected to the opposite end 26 of the micro flow channel 11 from the reservoir 21. The provision of the tube pump 35 permits the tested fluid to flow from the reservoir 21 and to circulate in the micro flow channel 11. Also, the resonance caused by the oscillator 28 homogenizes the density distribution of antigens in the tested fluid, and accordingly, the rate of antigens reacting to the antibodies in the reaction part 12 increases. Consequently, the reaction efficiency is improved. This fluid circulating type is especially advantageous when the volume of the tested fluid is large.

Fourth Embodiment; See FIGS. 5 and 6

Figure 5:
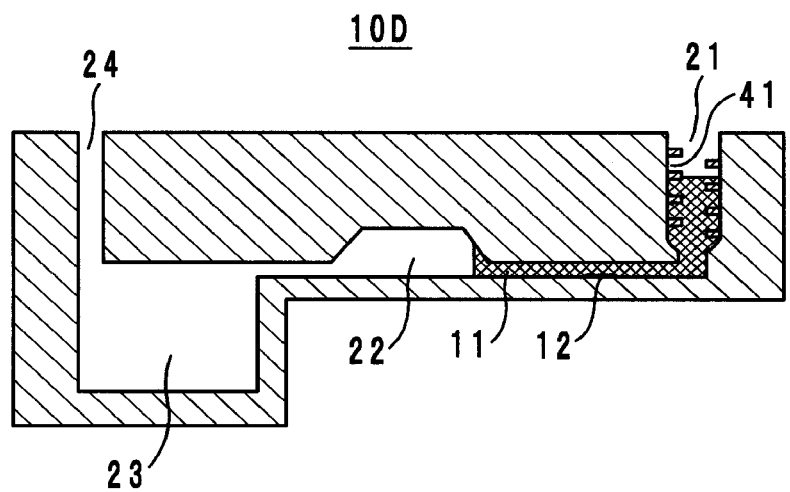
FIG. 5 is a sectional view of a test device according to a fourth embodiment of the present invention.

A test device 10D according to a fourth embodiment of the present invention, as shown in FIG. 5, is basically of the same structure as the test device 10A according to the first embodiment. The test device 10D according to the fourth embodiment, however, has a spiral groove 41 made in an inner wall of the first reservoir 21. As already described in connection with the first embodiment, the tested fluid is reciprocated between the reservoirs 21 and 22. According to the fourth embodiment, while the tested fluid flows in the spiral groove 41 in the first reservoir 21, the tested fluid is stirred, and the density distribution of the antigens in the tested fluid is homogenized. It is preferred that the upper opening of the reservoir 21 is wide so that the stirring of the tested fluid will be easy. In order to obtain a sufficient effect of a wide opening of the reservoir 21, the area of the upper opening of the reservoir 21 shall be set equal to or greater than 1/10 of the area of the planar projection of a sphere having a volume equal to that of the tested fluid.

Figure 6:
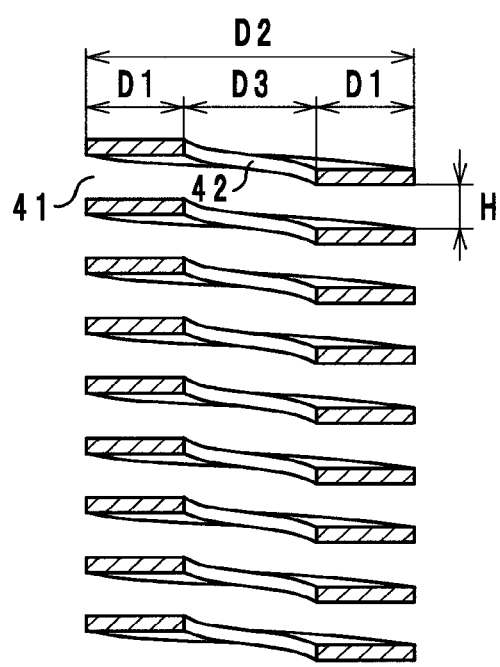
FIG. 6 is a sectional view of a spiral groove used in the fourth embodiment.

The spiral groove 41 is made by a plate shown by FIG. 6. The number of turns of the spiral groove 41 may be set arbitrarily. For efficient stirring of the tested fluid, the width D1 of the groove 41, that is, (the outer diameter D2–the inner diameter D1)/2 is preferably larger than the pitch H of the spiral groove 41. In the reservoir 21 of this structure, the flow drag in the spiral groove 41 is smaller than the flow drag in a central hole 42, and therefore, most part of the tested fluid passes through the groove 41. Accordingly, the stirring efficiency of the tested fluid is improved.

As shown in FIG. 6, the cross section of the plate forming the spiral groove 41 is rectangular. The plate may be disposed to tilt downward or may have round corners, so that the volume of residual fluid after a flow-out of the tested fluid can be reduced.

Fifth Embodiment; See FIG. 7

Figure 7:
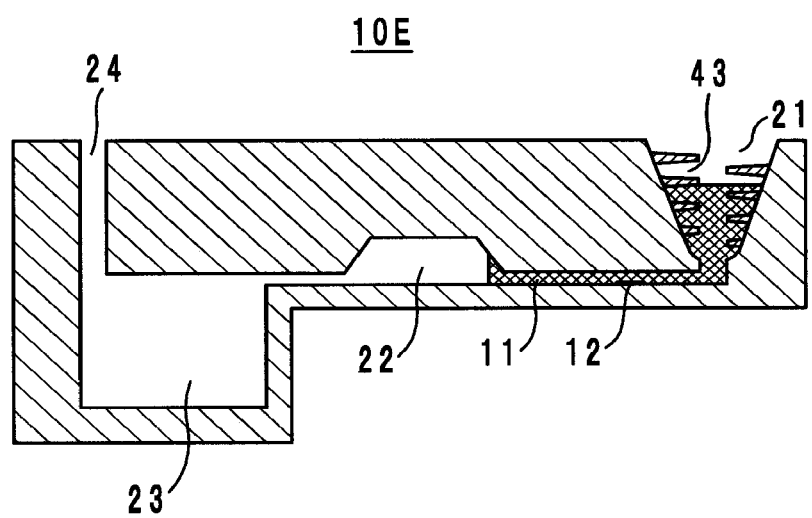
FIG. 7 is a sectional view of a test device according to a fifth embodiment of the present invention.

A test device 10E according to a fifth embodiment, as shown in FIG. 7, has a spiral groove 43 made in the inner wall of the reservoir 21, and a plate forming the spiral groove 43 has a rectangular cross section with a tapered side near the center of the reservoir 21. The test device 10E according to the fifth embodiment operates in the same way as the test device 10A according to the first embodiment and as the test device 10D according to the fourth embodiment, and the test device 10E has the same advantages as the test device 10A and the test device 10D.

Sixth Embodiment; See FIG. 8

Figure 8:
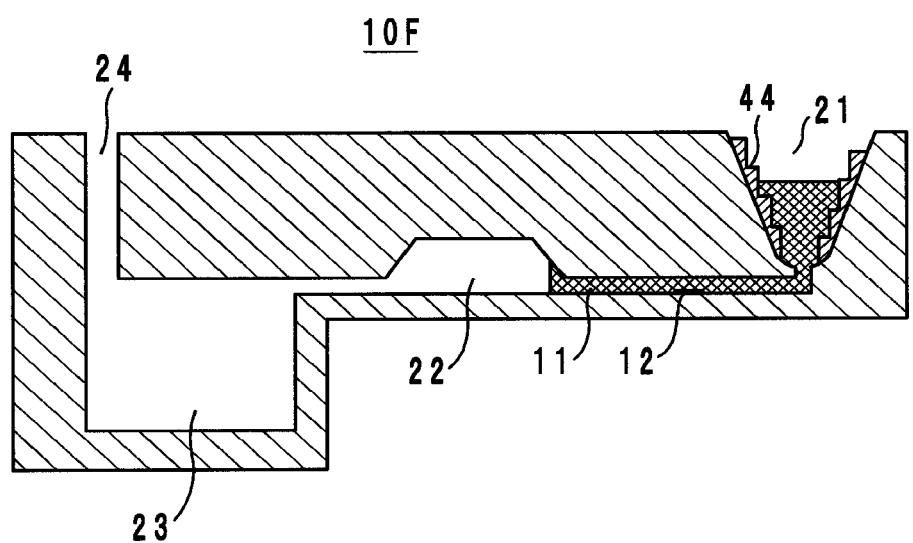
FIG. 8 is a sectional view of a test device according to a sixth embodiment of the present invention.
Figure 9:
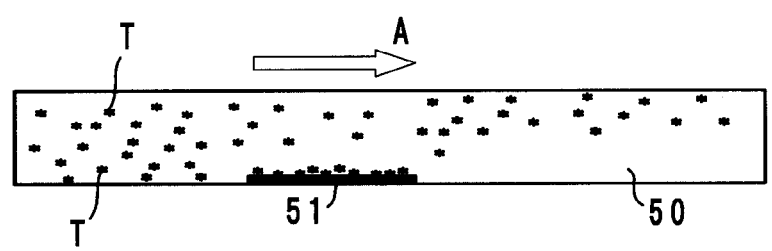
FIG. 9 is an illustration showing flow of a tested fluid in a conventional fluid sending system.

A test device 10F according to a sixth embodiment, as shown in FIG. 8, is basically of the same structure as the test device 10A according to the first embodiment. The test device 10F according to the sixth embodiment, however, has steps 44 on the inner wall of the reservoir 21. In the sixth embodiment, the tested fluid in the reservoir 21 is stirred by the steps 44, and thereby, the density distribution of the antigens in the tested fluid is homogenized.

OTHER EMBODIMENTS

Test devices, reaction apparatuses and reactive test methods according to the present invention are not limited to the embodiment above, and various changes and modifications are possible.

With respect to reactions at the reaction part, various kinds of reactions as well as immune reactions between antigens and antibodies may be carried out. However, in cases of immune reactions between antigens and antibodies, the molecules of antigens are of relatively large sizes and are hard to voluntarily spread, and moving a tested fluid forcibly to homogenize the density distribution of antigens in the tested fluid as disclosed by the present invention is very advantageous.

The oscillator for vibrating the tested fluid is not necessarily bonded to the test device, and the oscillator may be a piezoelectric actuator, an electromagnetic actuator or the like that is laid on the test device from the outside. The oscillator may be provided for the second reservoir. Alternatively, for both of the first reservoir and the second reservoir, oscillators may be provided. Also, the oscillator is not necessarily to vibrate only a part of the test device but may be to vibrate the test device entirely.

With respect to the way of detecting the reaction, as well as detection by use of optical characteristics, detection by use of electrical characteristics and visible detection by use of colors are possible. The detection means may be included in the reaction apparatus or may be structured separate from the reaction apparatus. Also, as auxiliary components of an optical detection system, a lens, a waveguide, a prism, etc. may be incorporated in the test device.

Also, in order to improve the detection efficiency, a fluorescently-labeled substance or the like may be used. More specifically, in a case of immune reaction between a fixed antibody (solid-phase antibody) and an antigen, a labeled antibody is prepared by labeling the antibody that is reactive specifically to the antigen with a fluorescent substance beforehand.

Other optional ways are possible. For example, after the antigen reacts to the solid-phase antibody and is caught in the reaction part, a solution containing the labeled antibody may be sent to the reaction part, and thereby, the antigen caught in the reaction part can be labeled with the fluorescent substance. In another way, the antigen is caused to react to the fluorescently-labeled antibody beforehand to generate a fluorescently-labeled complex, and the complex is sent to the reaction part so that reaction between the solid-phase antibody and the antigen can be detected easily. In these cases where a solution containing the labeled antibody or the labeled complex of the antigen and the antibody is sent in the micro flow channel, by homogenizing the density of the labeled antibody or the labeled complex in the solution during a plurality of reciprocal motions, the reaction efficiency can be improved.

There are some optional ways of vibrating the tested fluid so as to homogenize the density distribution of the tested chemical in the tested fluid. For example, a stirrer (a magnetic rotator) is provided in the micro flow channel including the reaction part, in at least one of the upstream portion or the downstream portion, and the stirrer is rotated by rotation of a magnet disposed outside of the test device or by turn on/off of an electric magnet so as to stir the tested fluid. Magnetic beads may be used instead of the stirrer.

In another way, ceramic particles that have a larger specific gravity than the tested fluid are put in the micro flow channel including the reaction part, in at least one of the upstream portion and the downstream portion, and the particles in the micro flow channel are vibrated by vibrations applied from the outside of the test device. Further, in another way, an electrode is disposed in the micro flow channel, in at least one of the upstream portion and the downstream portion, and an alternating current is applied to the electrode so as to vibrate ions and other substances with electric characteristics in the tested fluid. In this case, when an alternating current is applied to the electrode, the tested chemical itself, such as an antigen, is moved in the tested fluid by the electric force.

Although the present invention has been described in connection with the preferred embodiments above, it is to be noted that various changes and modifications are possible to those who are skilled in the art. Such changes and modifications are to be understood as being within the scope of the invention.

What is claimed is:

1. A reactive test method comprising:
    sending a tested fluid in a micro flow channel a plurality of times, the micro flow channel disposed oriented horizontally, the micro flow channel including a reaction part having a reactant fixed to a bottom of the micro flow channel thereat, wherein the reactant is reactive to a tested chemical dispersed in the tested fluid;
    actuating the tested fluid to move in at least one of two opposite sides of the micro flow channel so as to homogenize a density distribution of the tested chemical in the tested fluid, and
    stirring, via one or more of an oscillator, a resonator, or a spiral groove formed in the micro flow channel, the tested chemical and the tested fluid, wherein the oscillator, the resonator, or the spiral groove is disposed in at least one of two opposite sides of the micro flow channel.

2. A reactive test method according to claim 1, wherein the tested fluid is reciprocated in the micro flow channel.

3. A reactive test method according to claim 1, wherein the tested fluid is circulated.

4. A reactive test method according to claim 1, wherein the actuating the tested fluid is carried out in a reservoir that is disposed in at least one of two opposite sides of the micro flow channel, the reservoir having an inner volume larger than a volume of the tested fluid.

5. A reactive test method according to claim 1, wherein an immune reaction between an antigen in the tested fluid and an antibody fixed in the reaction part as the reactant is carried out in the reaction part.

* * * * *